United States Patent
Muerner et al.

(10) Patent No.: US 7,132,000 B2
(45) Date of Patent: Nov. 7, 2006

(54) AGENTS FOR OXIDATIVELY DYING KERATIN FIBERS

(75) Inventors: Hansruedi Muerner, Ursen (CH);
Manuela Javet, Marly (CH);
Dominique Le Cruer, Farvagny (CH)

(73) Assignee: Wella AG, Darmstadt (DE)

( * ) Notice: Subject to any disclaimer, the term of this patent is extended or adjusted under 35 U.S.C. 154(b) by 319 days.

(21) Appl. No.: 10/486,548

(22) PCT Filed: Dec. 12, 2002

(86) PCT No.: PCT/EP02/14113
§ 371 (c)(1),
(2), (4) Date: Feb. 9, 2004

(87) PCT Pub. No.: WO03/090700
PCT Pub. Date: Nov. 6, 2003

(65) Prior Publication Data
US 2004/0187226 A1 Sep. 30, 2004

(30) Foreign Application Priority Data
Apr. 26, 2002 (DE) ................. 102 18 588

(51) Int. Cl.
*A61K 7/13* (2006.01)
(52) U.S. Cl. .............. 8/405; 8/406; 8/407; 8/410; 8/411; 8/421; 8/608
(58) Field of Classification Search ............. 8/405, 8/406, 407, 410, 411, 421, 608
See application file for complete search history.

(56) References Cited

U.S. PATENT DOCUMENTS

| 3,904,357 | A |   | 9/1975 | Kinney ................ 8/10.2 |
| 4,797,130 | A | * | 1/1989 | Clausen et al. .......... 8/421 |
| 4,932,977 | A | * | 6/1990 | Schultz ................. 8/423 |
| 5,034,014 | A |   | 7/1991 | Wenke ................... 8/408 |

FOREIGN PATENT DOCUMENTS

| CA | 2 288 055 | 10/1998 |
| DE | 28 30 497 | 1/1980 |
| DE | 29 32 489 | 6/1980 |
| DE | 197 17 224 | 10/1998 |
| DE | 197 17 280 | 10/1998 |
| DE | 198 10 887 | 9/1999 |
| DE | 100 48 922 | 4/2002 |
| EP | 0 820 759 | 1/1998 |
| EP | 0 820 760 | 1/1998 |
| JP | 63243020 | 10/1988 |
| WO | 02/22092 | 3/2002 |
| WO | 02/051373 | 7/2002 |

OTHER PUBLICATIONS

English translation of the abstract of the Japanese Patent JP 63243020 A.*
"Spot Tests in Organic Analysis" by Fritz Feigl et al, Elsevier Publishing Company, Amsterdam London New York, 1966, pp. 198-205.
"Determination of Formaldehyde Using. . ." by N. P. Evmiridis et al, Analyst, Jun. 1987, vol. 11, pp. 831-835.
"Determination of Formaldehyde using a Kinetic. . ." by N. P. Evmiridis, et al, Analyst, Aug. 1990, vol. 115, pp. 1103-1107.
J.C. Thompsen: "Kinetic Studies of the Promoting. . ." Anal. Chem. 1984, 56, pp. 2834-2836. (In English).
W. Umbach: "Kosmetik—Entwicklung, Herstellung. . ." 1988, Georg Thieme Verlag, Stuttgart, pp. 287-289.

* cited by examiner

*Primary Examiner*—Eisa Elhilo
(74) *Attorney, Agent, or Firm*—Michael J. Striker

(57) ABSTRACT

Agent for oxidative dyeing of keratin fibers based on developers and couplers and containing at least one aldehyde of general formula (I) or (II)

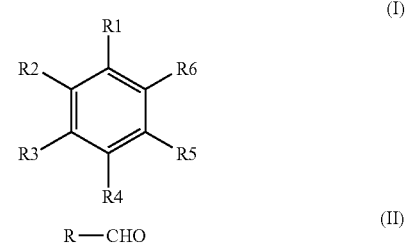

as well as the use of the aldehydes of formula (I) or (II) for increasing the color intensity of oxidative colorants and/or for shortening the time of exposure to oxidative colorants.

14 Claims, No Drawings

AGENTS FOR OXIDATIVELY DYING KERATIN FIBERS

The present invention relates to special aldehyde-containing agents for oxidative dyeing of keratin fibers and to the use of said aldehydes for accelerating the formation of oxidation dyes.

Oxidation dyes have attained substantial importance in the field of keratin fiber dyeing and particularly hair dyeing. The color is generated by reaction of certain developers with certain couplers in the presence of an appropriate oxidant. The developers used for this purpose are, in particular, 2,5-diaminotoluene, 2,5-diaminophenylethyl alcohol, p-aminophenol, 1,4-diaminobenzene and 4,5-diamino-1-(2-hydroxyethyl)pyrazole, whereas suitable couplers are, for example, resorcinol, 2-methylresorcinol, 1-naphthol, 3-aminophenol, m-phenylenediamine, 2-amino-4-(2'-hydroxyethyl)aminoanisole, 1,3-diamino-4-(2'-hydroxyethoxy)benzene and 2,4-diamino-5-fluorotoluene.

In addition to being able to produce colors of the desired intensity, oxidation dyes used for dyeing human hair must meet many other requirements. For example, such dyes must be unobjectionable from a toxicological and dermatological standpoint, and the hair colorations obtained must be highly resistant to light, permanent waving, acids and rubbing. In any case, however, in the absence of exposure to light, rubbing and chemical agents such colorations must remain stable for a period of at least 4 to 6 weeks. Moreover, it must be possible, by a combination of suitable developers and couplers, to produce a wide range of different color shades.

To attain a satisfactory dyeing result, the exposure time to conventional hair colorants is from 20 to 40 minutes. This time can be shortened by the application of heat. There are practical limits, however, concerning compatible temperatures and uniformity of the heat action. Shorter application times leading to the same dyeing result can also be achieved by increasing the initial concentration of the dye precursors, but such an increase in concentration is undesirable from the standpoint of the solubility, toxicology and dermatology of the ingredients and, last but not least, cost. Hence, a need continues to exist for new agents and methods which compared to the common oxidative colorants require a much shorter time to produce a good dyeing result and, in addition, do not cause a change in color shade.

We have now found that by adding certain aldehydes of general formula (I) or (II) to common oxidative hair colorants these requirements can be met to an unusually high degree. By use of small amounts of suitable aldehydes, the exposure times for attaining a given depth of shade can be significantly reduced.

The self-condensation of p-phenylenediamines to oligomers in the presence of an aldehyde is known from the literature. For example, in "Spot Tests in Organic Analysis" (7th ed., Elsevier, New York, 1966), F. Feigel describes an identification test for aldehyde groups which involves adding hydrogen peroxide and p-phenylenediamine reagents to an unknown substance diluted in a neutral or acidic solution. If the unknown substance contains an aldehyde function, a black color or black precipitate is formed. This type of reaction was studied kinetically by J. C. Thompsen and H. A. Mottola (Anal. Chem. 1984, 56, 2834–2836) at pH=5 in a system containing p-phenylenediamine, hydrogen peroxide and glutaraldehyde. Quantitative methods for measuring formaldehyde based on this type of reaction have been described by N. P. Evmiridis and M. I. Karayannis (Analyst 1987, 112, 831–835), and by N. P. Evmiridis, N. C. Sadiris and M. I. Karayannis, Analyst 1990, 115, 1103–1107). This work included besides the self-condensation of p-phenylenediamine also analogous reactions with N-methyl-substituted p-phenylenediamines. In both cases, the analytical methods showed the best detection limits and reproducibility in a weakly acidic range (pH 5.5–6.0). Also known from the literature is the use of cinnamaldehyde and hydroxybenzaldehyde in oxidative hair colorants, but a shortening of the exposure time by addition of an aldehyde is not described. On this matter, the reader is referred to U.S. Pat. No. 5,034,014, European Unexamined Patent Applications 0820759 and 0820760 and German Examined Patent Applications 28 30497 and 29 32489.

We have now found that certain aldehydes accelerate not only the self-condensation of p-phenylenediamine, but also—and particularly in a neutral or basic medium—the reaction of a developer with a coupler in oxidative dye systems. By aldehyde addition, the exposure time needed to attain a certain depth of color shade can thus be clearly reduced.

Hence, the object of the present invention are agents for oxidative dyeing of keratin fibers based on developers and couplers and containing at least one aldehyde of general formula (I) or (II)

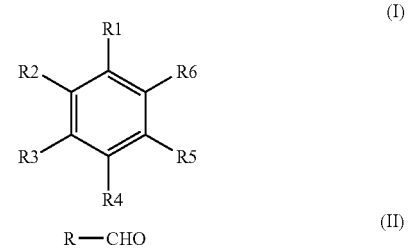

wherein

R1, R2, R3, R4, R5 independently of each other denote hydrogen, a carboxyl group, an aldehyde group, a halogen atom (F, Cl, Br, I), a cyano group, a hydroxyl group, a ($C_1$–$C_4$)-alkoxy group, a ($C_2$–$C_4$)-hydroxyalkoxy group, a ($C_1$–$C_6$)-alkyl group, a nitro group, a ($C_1$–$C_4$)-alkylamino group, a di($C_1$–$C_4$)-alkylamino group, a [($C_2$–$C_4$)-dihydroxyalkyl]amino group, a [($C_1$–$C_4$) -hydroxyalkyl]-($C_1$–$C_4$)-alkylamino group, a trifluoromethyl group, a ($C_1$–$C_4$)-hydroxyalkyl group or a ($C_2$–$C_4$)-dihydroxyalkyl group, or two adjacent R1 to R5 groups form an —O—$CH_2$—O— bridge;

R6 denotes a —CH=CH—CHO group, a —CHO group or a —X—(Y)$_r$—Z—CHO group (with r=0 or 1);

R denotes a —CR7R8R9 group, a saturated, optionally substituted cycloalkyl group with 3 to 10 atoms in the ring, the ring possibly containing up to three heteroatoms from the group consisting of nitrogen, oxygen and sulfur, or an optionally substituted cycloalkene group with 3 to 10 atoms in the ring, the ring possibly containing up to three cumulated or non-cumulated double bonds and up to three heteroatoms from the group consisting of nitrogen, oxygen and sulfur;

R7, R8 and R9 can be equal or different and independently of each other denote hydrogen, a saturated cycloalkyl group with 3 to 10 atoms in the ring, the ring possibly containing up to 3 heteroatoms from the group consisting of nitrogen, oxygen and sulfur, a cycloalkene group with 3 to 10 atoms in the ring, the ring possibly containing up to three cumulated or non-cumulated double bonds and up to three heteroatoms from the group consisting of nitrogen, oxygen and sulfur, a branched or unbranched —$(CH_2)_n$-alkyl chain with n equal to an integer from 1 to 20, a branched or unbranched —$(CH_2)_m$—$(CH=CH)_p$—$(CH_2)_q$ alkene chain where m and q independently of each other stand for an integer from 0 to 20 and p stands for an integer from 1 to 5, or a branched or unbranched —$(CH_2)_m$—$(C≡C)_p$—$(CH_2)_q$ alkyne chain where m and q independently of each other stand for an integer from 0 to 20 and p stands for an integer from 1 to 3, the aforesaid groups optionally being substituted with one or more halogen atoms, hydroxyl groups, sulfonic acid groups, carbonyl groups (keto groups or aldehyde groups), carboxyl groups, ester groups, amido groups, thioester groups, ether groups, thioether groups, nitro groups, cyano groups, amino groups, di($C_1$–$C_4$)-alkylamino groups, [dihydroxy-($C_2$–$C_4$)-akly]amino groups, [($C_1$–$C_4$)-hydroxyalkyl]-($C_1$–$C_4$)-alkylamino groups, trifluoromethyl groups or phosphate groups;

X and Z can be equal or different and independently of each other denote a branched or unbranched —$(CH_2)_n$-alkyl chain with n equal to an integer from 1 to 20, a branched or unbranched —$(CH_2)_m$—$(CH=CH)_p$—$(CH_2)_q$ alkene chain where m and q independently of each other stand for an integer from 0 to 20 and p stands for an integer from 1 to 5, or a branched or unbranched —$(CH_2)_m$—$(C≡C)_p$—$(CH_2)_q$ alkyne chain where m and q independently of each other stand for an integer from 0 to 20 and p stands for an integer from 1 to 3, and Y denotes —O—, —S—, —NH—, NR— or a —C(O)—O—, —O—C(O)—, —C(O)—NH— or —O—C=NH— group;

the —X—$(Y)_r$Z group possibly denoting a saturated cycloalkane ring with 3 to 7 atoms in the ring, and depending on the ring size containing up to three heteroatoms from the group consisting of nitrogen, oxygen and sulfur, a cycloalkene ring with up to two cumulated or non-cumulated double bonds and 3 to 7 atoms in the ring, and depending on ring size up to three heteroatoms from the group consisting of nitrogen, oxygen and sulfur;

provided that in formula (I), when R6 denotes a —CH=CH—CHO group or a —CHO group at least two adjacent R1 to R5 groups form an —O—$CH_2$—O— bridge.

For purposes of the present patent application, keratin fibers are, for example, wool, silk or hair and particularly human hair.

Preferred compounds of formula (I) are those wherein R6 denotes an X—$(Y)_r$-Z-CHO group (with r=0 or 1), the X—$(Y)_r$-Z grouping denoting a branched or unbranched —$(CH_2)_n$ alkyl chain with n equal to an integer from 1 to 12, a branched or unbranched —$(CH_2)_m$—$(CH=CH)_p$—$(CH_2)_q$ alkene chain wherein the sum of m and q is less than or equal to 20 and p stands for an integer from 1 to 3 or a branched or branched $(CH_2)_m$—$(C≡C)_p$—$(CH_2)_q$-alkene chain wherein the sum of m and q is less than or equal to 20 and p is an integer from 1 to 3, or the X—$(Y)_r$-Z grouping denotes a saturated cycloalkane ring with 3 to 7 atoms in the ring and depending on ring size the ring containing up to 3 heteroatoms from the group consisting of nitrogen, oxygen and sulfur, or a cycloalkene ring with up to two cumulated or non-cumulated double bonds and 3 to 7 atoms in the ring, and depending on ring size the ring containing up to 3 heteroatoms from the group consisting of nitrogen, oxygen and sulfur; the aforesaid groups optionally being substituted with one or more halogen atoms, hydroxyl groups, sulfonic acid groups, carbonyl groups, carboxyl groups, ester groups, amido groups, thioester groups, ether groups, thioether groups, nitro groups, cyano groups, amino groups, di($C_1$–$C_4$)-alkylamino groups, [dihydroxy($C_2$–$C_4$)-alkyl]amino groups, [($C_1$–$C_4$)-hydroxyalkyl]-($C_1$–$C_4$)-alkylamino groups, trifluoromethyl groups or phosphate groups.

Preferred compounds of formula (II) are those wherein R denotes a saturated, optionally substituted cycloalkyl group with 3 to 10 atoms in the ring, the ring possibly containing up to three heteroatoams from the group consisting of nitrogen, oxygen and sulfur, or an optionally substituted cycloalkene group with 3 to 10 atoms in the ring, the ring possibly containing up to three cumulated or non-cumulated double bonds and up to three heteroatoms from the group consisting of nitrogen, oxygen and sulfur, or a —CR7R8R9 group with R7, R8 and R9 independently of each other denoting hydrogen, a saturated cycloalkane ring with 3 to 7 atoms in the ring and depending on ring size with up to three heteroatoms from the group consisting of nitrogen, oxygen and sulfur, a cycloalkene ring with up to two cumulated or non-cumulated double bonds and 3 to 7 atoms in the ring and depending on the ring size up to three heteroatoms from the group consisting of nitrogen, oxygen and sulfur, a branched or unbranched —$(CH_2)_n$ alkyl chain with n equal to an integer from 1 to 16, a branched or unbranched —$(CH_2)_m$—$(CH=CH)_p$—$(CH_2)_q$ alkene chain wherein the sum of m and q is less than or equal to 20 and p is equal to an integer from 1 to 3, or a branched or unbranched —$(CH_2)_m$—$(C≡C)_p$—$(CH_2)_q$ alkyne chain wherein the sum of m and q is less than or equal to 20 and p is equal to an integer from 1 to 3, the aforesaid groups optionally being substituted with one or more halogen atoms, hydroxyl groups, sulfonic acid groups, carbonyl groups, carboxyl groups, ester groups, amido groups, thioester groups, ether groups, thioether groups, nitro groups, cyano groups, amino groups, di($C_1$–$C_4$)-alkylamino groups, [dihydroxy-($C_2$–$C_4$)-alkyl]amino groups, [($C_1$–$C_4$)-hydroxyalkyl]-($C_1$–$C_4$)-alkylamino groups, trifluoromethyl groups or phosphate groups.

Particularly preferred compounds of formula (I) are those wherein R6 stands for a —X—$(Y)_r$—Z group (with r=0 or 1) which denotes a branched or unbranched —$(CH_2)_n$-alkyl chain with n equal to an integer from 1 to 10, a branched or unbranched —$(CH_2)_m$—$(CH=CH)_p$—$(CH_2)_q$ alkene chain wherein the sum of m and q is less than or equal to 12 and p is equal to an integer from 1 to 3, or a branched or unbranched —$(CH_2)_m$—$(C≡C)_p$—$(CH_2)_q$ alkyne chain wherein the sum of m and q is less than or equal to 12 and p is equal to an integer from 1 to 3, or the —X—Y—Z— group denotes a saturated cycloalkane ring with 5 or 6 atoms in the ring which depending on the ring size can contain up to three heteroatoms from the group consisting of nitrogen, oxygen and sulfur, or a cycloalkene ring with up to two cumulated or non-cumulated double bonds and 5 or 6 atoms in the ring, and depending on the ring size containing up to three heteroatoms from the group consisting of nitrogen, oxygen and sulfur, the aforesaid groups optionally being substituted with one or more halogen atoms, hydroxyl groups, sulfonic acid groups, carbonyl groups, carboxyl groups, ester groups, amido groups, thioester groups, ether groups, thioether groups, nitro groups, cyano groups, amino groups, di($C_1$–$C_4$)-alkylamino groups, [dihydroxy-($C_2$–$C_4$)-alkyl]amino groups, [($C_1$–$C_4$)-hydroxyalkyl]-($C_1$–$C_4$)-alkylamino groups, trifluoromethyl groups or phosphate groups.

Particularly preferred compounds of formula (II) are those wherein R denotes a saturated, optionally substituted (preferably with one or more ($C_1$–$C_4$)-alkyl groups) cycloalkyl group with 5 or 6 atoms in the ring, the ring possibly containing up to three heteroatoms from the group consisting of nitrogen, oxygen and sulfur, or an optionally substituted (preferably with one or more ($C_1$–$C_4$)-alkyl groups)

cycloalkene group with 5 or 6 atoms in the ring, the ring containing up to three cumulated or non-cumulated double bonds and up to three heteroatoms from the group consisting of nitrogen, oxygen and sulfur, or a —CR7R8R9— group with R7, R8 and R9 independently of each other denoting hydrogen, a saturated cycloalkane ring with 5 or 6 atoms in the ring, and which depending on the ring size contains up to three heteroatoms from the group consisting of nitrogen, oxygen and sulfur, a cycloalkene ring with up to two double bonds and 5 or 6 atoms in the ring, and depending on the ring size containing up to three heteroatoms from the group consisting of nitrogen, oxygen and sulfur, a branched or unbranched —$(CH_2)_n$-alkyl chain with n equal to an integer from 1 to 10, a branched or unbranched —$(CH_2)_m$—(CH=CH)$_p$—$(CH_2)_q$ alkene chain wherein the sum of m and q is less than or equal to 12 and p is equal to an integer from 1 to 3, or a branched or unbranched —$(CH_2)_m$—(C≡C)$_p$—$(CH_2)_q$ alkyne chain wherein the sum of m and q is less than or equal to 12 and p is equal to an integer from 1 to 3, the aforesaid groups optionally being substituted with one or more halogen atoms, hydroxyl groups, sulfonic acid groups, carbonyl groups, carboxyl groups, ester groups, amido groups, thioester groups, ether groups, thioether groups, nitro groups, cyano groups, amino groups, di($C_1$–$C_4$)-alkylamino groups, [dihydroxy-($C_2$–$C_4$)-alkyl]amino groups, [($C_1$–$C_4$)-hydroxyalkyl]-($C_1$–$C_4$)-alkylamino groups, trifluoromethyl groups or phosphate groups.

Suitable compounds of formula (I) are, in particular, 3-phenylbutyraldehyde, p-tert.butyl-α-methylhydrocinnamaldehyde, heliotropin, 2-methyl-3-(4'-ethylphenyl)propionaldehyde, 2-(phenylmethylene)heptanal, 3-(3'-isopropylphenyl)butanal, 2-methyl-3-(4'-isopropylphenyl)propionaldehyde, 2-(phenylmethylene)octanal and phenylethanal.

Suitable compounds of formula (II) are, in particular, acetaldehyde, propionaldehyde, butanal, pentanal, isopentanal, hexanal, heptanal, octanal, malonic dialdehyde, glutaraldehyde, 2,4-dimethyl-3-cyclohexenecarboxaldehyde, cyclohexanal, 3,7-dimethyl-7-hydroxyoctanal, cis/trans-3,7-dimethyl-2,6-octadienal, 3,7-dimethyl-6-octenal, (E,Z)-2,6-nonadienal, dimethyloctahydro-2-naphthaldehyde, 2-methylpentanal, 5-hydroxypentanal, 2-ethylhexanal, 3,5,5-trimethylhexanal, 2-ethylbutyraldehyde, 3,3-dimethylbutyraldehyde, 2-ethylbutyraldehyde, 2-methylbutyraldehyde, isobutyraldehyde, hydroxyisohexyl-3-cyclohexenecarboxaldehyde, 2,6,6-trimethyl-1,3-cyclohexadiene-1-carboxaldehyde and pinoacetaldehyde.

Suitable as compounds of formula (I) or (II) are also substances containing a masked or blocked aldehyde function. By this are meant compounds which by spontaneous elimination of protective groups are converted into molecules of general formula (I) or (II). Suitable protective groups are, for example, the hydrates of aldehyde functions, acetals and hemiacetals, anils, Schiff bases with aliphatic and aromatic amines, or sulfite adducts. Also suitable are compounds of the diazolidinyl, hydantoin or imidazolidinyl type as well as the oligomeric and polymeric forms of the individual aldehydes.

The aldehyde compounds of formula (I) or (II) are contained in the colorant of the invention in a total amount from about 0.005 to 20 wt. %, (based on the ready-to-use preparation) an amount from about 0.05 to 5 wt. % and particularly from 0.025 to 2.5 wt. % being preferred.

Suitable developers are, in particular, 1,4-diaminobenzene (p-phenylenediamine), 1,4-diamino-2-methylbenzene (p-toluylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(1-hydroxyethyl)benzene, 1,4-diamino-2-(2-hydroxyethyl)-benzene, 1,4-diamino-2-(1-methylethyl)benzene, 1,3-bis-[(4-aminophenyl)(2-hydroxyethyl)amino]-2-propanol, 1,4-bis-[(4-aminophenyl)amino]butane, 1,8-bis-(2,5-diaminophenoxy)-3,6-dioxoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-di-amino-1-methyl-1H-pyrazole, 2-aminophenol, 2-amino-6-methylphenol, 2-amino-5-methylphenol and 1,2,4-trihydroxybenzene.

Suitable couplers are, in particular, N-(3-dimethylaminophenyl)urea, 2,6-diaminopyridine, 2-amnino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamnino-2,6-dimethoxypyridine, 1,3-diaminobenzene, 2,4-diamino-1-(2-hydroxyethoxy)-benzene, 1,3-diamino-4-(2,3-dihydroxypropoxy)benzene, 1,3-diamino-4-(3-hydroxypropoxy)benzene, 1,3-diamino-4-(2-methoxyethoxy)benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophen oxyacetic acid, 3-[di(2-hydroxyethyl)amino]aniline, 4-amino-2-di[(2-hydroxyethyl)-amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4- amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, (m-dihydroxyphenyl)acrylamide, 1-chloro-2,4-dihydroxybenzene, 2-chloro-(m-dihydroxyphenyl)acrylamide, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)-amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

The couplers and developers can be contained in the colorant of the invention either individually or in admixture with each other, the total amount of couplers and developers in the colorant of the invention (based on the total amount of ready-to-use colorant) being from about 0.005 to 20 weight percent, preferably from about 0.01 to 5 weight percent and particularly from 0.1 to 2.5 weight percent, each.

The total amount of the developer-coupler combination contained in the colorant described herein is preferably from about 0.01 to 20 weight percent (based on the ready-to-use colorant), an amount from about 0.02 to 10 weight percent and particularly from 0.2 to 6 weight percent being especially preferred. In general, the developers and couplers are used in approximately equimolar amounts. However, it is not disadvantageous if the developers are present in a certain excess or deficiency with respect to such an amount.

Moreover, the colorant of the invention can also contain other dye components, for example 6-amino-2-methylphenol and 2-amino-5-methylphenol as well as common direct dyes, triphenylmethane dyes, aromatic nitro dyes, azo dyes and disperse dyes. The colorants of the invention can contain these dye components in an amount from about 0.1 to 4 weight percent (based on the ready-to-use colorant).

Naturally, the couplers and developers and the other dye components, provided they are bases, can also be used in the form of their physiologically compatible salts of organic or inorganic acids, for example hydrochloric acid or sulfuric acid, or—if they contain aromatic OH— groups—in the form of salts of bases, for example as alkali metal phenoxides.

Moreover, if the colorants are used for dyeing hair, they can also contain common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be formulated, for example, as a solution, particularly an aqueous or aqueous-alcoholic solution. A particularly preferred formulation, however, is a cream, gel or emulsion. Such a preparation consists of a mixture of dye components and additives commonly used for such preparations.

The agents of the invention can be in the form of a "one-component preparation" consisting of a dye carrier composition containing one of the compounds of formula (I) to (III) [sic] and being mixed with an oxidant before use or being allowed to become oxidized in the air by atmospheric oxygen ("air oxidation"), or in the form of a "multicomponent preparation" wherein the compounds of formula (I) or (II) and the other constituents of the dye carrier composition are separated from one another and are mixed only just before use (optionally by adding an oxidant).

Common additives to solutions, creams, emulsions or gels are, for example, solvents such as water, lower aliphatic alcohols, for example ethanol, propanol or isopropanol, glycerol or glycols such as 1,2-propylene glycol; moreover wetting agents or emulsifiers from the classes of anionic, cationic, amphoteric or nonionic surface-active substances such as, for example, the fatty alcohol sulfates, ethoxylated fatty alcohol sulfates, alkylsulfonates, alkylbenzenesulfonates, alkyltrimethyl-ammonium salts, alkylbetaines, ethoxylated fatty alcohols, ethoxylated nonylphenols, fatty alkanolamides and ethoxylated fatty esters, furthermore thickeners such as the higher fatty alcohols, starch, cellulose derivatives, petrolatum, paraffin oil and fatty acids; moreover hair-care agents such as cationic resins, lanolin derivatives, cholesterol, pantothenic acid and betaine. The said constituents are used in amounts commonly employed for such purposes, for example the wetting agents and emulsifiers at a concentration from about 0.5 to 30 weight percent, the thickeners in an amount from about 0.1 to 30 weight percent and the hair-care agents at a concentration from about 0.1 to 5 weight percent.

Depending on the composition, the colorant of the invention can be weakly acidic, neutral or alkaline. In particular, it has a pH from 6.5 to 11.5, the adjustment to a basic value preferably being achieved with ammonia. However, organic amines, for example monoethanolamine or triethanolamine, or inorganic bases, for example sodium hydroxide or potassium hydroxide can also be used. For pH adjustment in the acidic range, an inorganic or organic acid, for example phosphoric acid, acetic acid, citric acid or tartaric acid, can be used.

For use in oxidative dyeing of hair, the afore-described colorant is mixed with an oxidant just before use and the resulting mixture is applied to the hair in an amount sufficient for the hair treatment, in general in an amount from about 60 to 200 grams, depending on the fullness of the hair.

Suitable oxidants for developing the hair coloration are mainly hydrogen peroxide or the compounds of addition thereof to urea, melamine, sodium borate or sodium carbonate in the form of a 3 to 12%, preferably 6% aqueous solution. Atmospheric oxygen can also be used. If a 3 to 6% hydrogen peroxide solution is used as oxidant, the weight ratio of hair colorant to oxidant is from 5:1 to 1:5, preferably 2:1 to 1:3 and particularly 1:1. Larger amounts of oxidant are used primarily at higher dye concentrations in the hair colorant or when more pronounced hair bleaching is wanted at the same time.

In principle, adding other oxidants, for example persulfate salts is just as possible as the use of atmospheric oxygen.

The mixture is allowed to act on the hair at 15 to 50° C. for about 10 to 45 minutes, preferably for 10 to 20 minutes, after which the hair is rinsed with water and dried. Following this rinsing, the hair may be additionally washed with a shampoo and optionally post-rinsed with a weak organic acid, for example citric acid or tartaric acid. The hair is then dried.

The colorant of the invention gives within a very short time colorations of excellent color stability, particularly in terms of light fastness, wash fastness and rubbing fastness. As far as the coloring properties are concerned, depending on the kind and composition of the dye components, the colorant of the invention provides a wide range of different color shades ranging from blond to brown, purple, violet, blue and black. Said shades stand out by their unusual color intensity. Furthermore, the very good coloring properties of the colorant of the present patent application are, in particular, characterized by the fact that this colorant also makes it possible to dye gray, chemically not previously damaged keratin fibers, particularly human hair, with good covering power and without any problems.

The following examples are intended to illustrate the subject matter of the invention more closely without limiting its scope.

EXAMPLES

Example 1

Hair Colorant Solution

Hair colorant solutions of the following composition were prepared:

| 0.01 mol | of 4-amino-3-methylphenol |
| 0.01 mol | of 3-amino-6-methylphenol |
| 0.3 g | of disodium ethylenediaminetetraacetate |
| 0.3 g | of ascorbic acid |
| 2.8 g | of lauryl ether sulfate |
| 8.0 g | of ethanol, 96% |
| 9.0 g | of ammonia, 25% aqueous solution |
| to 100.0 g | water |

Just before use, 20 g of the above colorant solution was mixed with 20 g of a 6% aqueous hydrogen peroxide solution and 1.0 g of an "accelerator solution" as per Table 1. The resulting mixture (pH=9.5–10) was then applied to bleached hair and after an exposure time of 10 minutes at 40° C., the hair was rinsed with water. The hair was then washed with a commercial shampoo and dried.

Table 1 summarizes the dyeing results obtained.

TABLE 1

| "Accelerator Solution" | L* | a* | b* |
|---|---|---|---|
| a) Water (not according to invention) | 56.0 | 30.1 | 24.6 |
| b) 5% acetaldehyde in ethanol:water, 1:1 | 39.3 | 38.6 | 26.2 |
| c) 5% hexanal in ethanol:water, 1:1 | 43.8 | 37.2 | 26.6 |
| d) 2% glutaraldehyde in water | 40.3 | 38.4 | 27.0 |
| e) 5% hydroxycitronellal in ethanol:water, 1:1 | 42.5 | 38.9 | 25.5 |
| f) 5% 3-phenylbutyraldehyde in ethanol | 45.3 | 44.3 | 29.3 |

The color values in Table 1 show unequivocally that the addition of an aldehyde of the invention results in a coloration of higher intensity (lower L-value) than that obtained with an agent not according to the invention.

Example 2

Hair Colorant Solution

Hair colorant solutions of the following composition were prepared:

| 0.01 mol | of a developer as per Table 2 |
| 0.01 mol | of a coupler as per Table 2 |
| 0.3 g | of disodium ethylenediaminetetraacetate |
| 0.3 g | of ascorbic acid |
| 2.8 g | of lauryl ether sulfate |
| 8.0 g | of ethanol, 96% |
| 9.0 g | of ammonia, 25% aqueous solution |
| to 100.0 g | water |

Just before use, 20 g of the above colorant solution was mixed with 20 g of a 6% aqueous hydrogen peroxide solution and (A) 1.0 g of water (not according to the invention) or (B) 1.0 g of 1% aqueous glutaraldehyde solution (according to the invention). The resulting mixture (pH=9.5–10) was then applied to bleached hair and after an exposure time of 10 minutes at 40° C., the hair was rinsed with water. The hair was then washed with a commercial shampoo and dried.

Table 2 summarizes the dyeing results obtained.

TABLE 2

| Developer-Coupler Combination | (A) Not According to the invention | | | (B) According to the Invention | | |
|---|---|---|---|---|---|---|
| | L* | a* | b* | L* | a* | b* |
| a) 1,4-Diamino-2-methylbenzene/resorcinol | 44.6 | 2.6 | 18.6 | 36.5 | 2.9 | 17.0 |
| b) 4,5-Diamino-1-(2-hydroxyethyl)-1H-pyrazole/3-amino-6-methylphenol | 49.3 | 43.4 | 35.6 | 44.6 | 45.9 | 36.8 |
| c) 1,4-Diamino-2-3-aminophenol | 45.3 | 4.7 | 3.8 | 38.4 | 6.2 | 1.8 |
| d) 4-Amino-3-methylphenol/3-amino-6-methylphenol | 59.1 | 28.2 | 22.8 | 42.7 | 37.1 | 27.3 |
| e) 1,4-Diamino-2-methylbenzene/3-amino-6-methylphenol | 30.9 | 20.0 | −6.8 | 24.3 | 17.0 | −5.0 |

The color values in Table 2 show unequivocally that by addition of an aldehyde according to the invention, regardless of the developer-coupler combination used, a coloration of higher color intensity (lower L-value) is obtained than with an agent not according to the invention.

Example 3

Hair Colorant Cream

A hair colorant cream of the following composition was prepared:

| 0.002 mol | of 2-amino-4-hydroxyethylaminoanisole |
| 0.016 mol | of 4-amino-3-methylphenol |
| 0.011 mol | of 3-amino-6-methylphenol |
| 0.002 mol | of 1-naphthol |
| 10.8 g | of cetylstearyl alcohol |
| 2.5 g | of lauryl ether sulfate |
| 0.3 g | of disodium ethylenediaminetetraacetate |
| 0.3 g | of ascorbic acid |
| 18.0 g | of ethanol, 96% |
| 7.5 g | of ammonia, 25% aqueous solution |
| to 100.0 g | water |

Just before use, 20 g of the above colorant solution was mixed with 20 g of a 6% aqueous hydrogen peroxide solution and (A) 0.4 g of water (not according to the invention) or (B) 0.4 g of 10% aqueous glutaraldehyde solution (according to the invention). The resulting mixture (pH=9.5–10) was then applied to bleached hair and after an exposure time of 20 and 30 minutes, respectively, at 40° C., the hair was rinsed with water. The hair was then washed with a commercial shampoo and dried.

Table 3 summarizes the dyeing results obtained.

TABLE 3

| Exposure Time | (A) Not According to the Invention | | | (B) According to the Invention | | |
|---|---|---|---|---|---|---|
| | L* | a* | b* | L* | a* | b* |
| 20 minutes | 33.0 | 29.6 | 17.46 | 28.3 | 26.2 | 14.8 |
| 30 minutes | 29.3 | 27.1 | 15.1 | 24.8 | 24.1 | 12.5 |

The color values in Table 3 show unequivocally that the addition of an aldehyde of the invention produces a coloration of higher intensity (lower L-value) already after 20 minutes than does an agent not according to the invention after 30 minutes.

The L*a*b* values in Tables 1 to 3 were measured with a Minolta model CR-200 color meter. The L-value indicates brightness (namely the lower the L-value the higher is the color intensity), and the a-value is a measure of the red content of the color (namely the higher the a-value, the higher is the red content). The b-value is a measure of the blue content of the color, the blue content being the higher the more negative the b-value.

Unless otherwise indicated, all percentages given in the present patent application are by weight.

The invention claimed is:

1. An agent for oxidative dyeing of keratin fibers, said agent comprising (i) at least one developer substance; (ii) at least one coupler substance:

wherein said at least one coupler substance is selected from the group consisting of N-(3-dimethylaminophenyl)urea; 2,6-diaminopyridine; 2-amino-4-[(2-hydroxyethyl)amino]anisole; 2,4-diamino-1-fluoro-5-methylbenzene; 2,4-diamino-1-methoxy-5-methylbenzene; 2,4-diamino-1-ethoxy-5-methylbenzene; 2,4-diamino-1-(2-hydroxyethoxy)-5-methylbenzene; 24-di[(2-hydroxy-ethyl)amino]-1,5-dimethoxybenzene; 2,3-diamino-6-methoxypyridine; 3-amino-6-methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-dihydroxypropoxy)benzene; 1,3-diamino-4-(3-dihydroxypropoxy)benzene; 1,3-diamino-4-(2-methoxyethoxy)-benzene; 2,4-diamino-1,5-di(2-hydroxyethoxy)benzene; 1-(2-aminoethoxy)-2,4-diaminobenzene; 2-amino-1-(2-hydroxyethoxy)-4-methylaminobenzene; 2,4-diaminophenoxyacetic acid; 3-[di(2-hydroxyethyl)amino]aniline; 4-amino-2-di[(2-hydroxyethyl)amino]-1-ethoxybenzene; 5-methyl-2-(1-methylethyl)phenol; 3-[(2-hydroxyethyl)amino]aniline; 3-[(2-aminoethyl)amino]aniline; 1,3-di-(2,4-diaminophenoxy)propane; di(2,4-diaminophenoxy)methane;

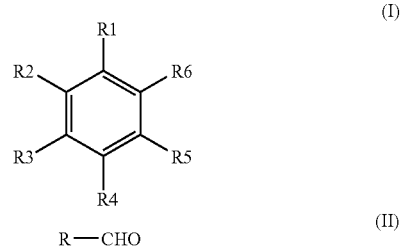

wherein R1, R2, R3, R4, and R5, independently of each other, denote hydrogen, a carboxyl group, an aldehyde group, a halogen atom, a cyano group, a hydroxyl group, a ($C_1$–$C_4$)-alkoxy group, a ($C_2$–$C_4$)-hydroxyalkoxy group, a ($C_1$–$C_5$)-alkyl group, a nitro group, a ($C_1$–$C_4$)-alkylamino group, a di($C_1$–$C_4$)-alkylamino group, a [($C_2$–$C_4$)-dihydroxyalkyl)]amino group, a [($C_1$–$C_4$)-hydroxyalkyl]-($C_1$–$C_4$)-alkylamino group, a trifluoromethyl group, a ($C_1$–$C_4$)-hydroxyalkyl group, or a ($C_2$–$C_4$)-dihydroxyalkyl group, or two adjacent R1 to R5 groups form an —O—$CH_2$—O— bridge;

R6 denotes a —CH=CH—CHO group, a —CHO group, or a —X(Y)$_r$—Z—CHO group with r=0 or1;

R denotes a —CR7R8R9 group; a saturated, optionally substituted cycloalkyl group with 3 to 10 atoms and optionally containing up to three heteroatoms selected from the group consisting of nitrogen, oxygen, and sulfur; or an optionally substituted cycloalkylene group with 3 to 10 atoms and optionally containing up to three cumulated or non-cumulated double bonds and up to three heteroatoms selected from the group consisting of nitrogen, oxygen, and sulfur; R7, R8, and R9 are the same or different and, independently of each other, denote hydrogen, a saturated cycloalkyl group with 3 to 10 atoms and optionally containing up to 3 heteroatoms selected from the group consisting of nitrogen, oxygen, and sulfur; a cycloalkylene group with 3 to 10 atoms and optionally containing up to three cumulated or non-cumulated double bonds and up to three heteroatoms selected from the group consisting of nitrogen, oxygen, and sulfur; a branched or unbranched —$(CH_2)_n$— group with n equal to an integer from 1 to 20; a branched or unbranched —$(CH_2)_m$—(CH=CH)$_p$—$(CH_2)_q$-alkene chain with m and q, independently of each other, denoting an integer from 0 to 20 and p denoting an integer from 1 to 5; or a branched or unbranched —$(CH_2)_m$—(C≡C)$_p$—$(CH_2)_q$-alkyne chain with m and q, independently of each other, denoting an integer from 0 to 20 and p denoting an integer from 1 to 3; wherein the foregoing R groups are optionally substituted with one or more halogen atoms, hydroxyl groups, sulfonic acid groups, carbonyl groups, carboxyl groups, ester groups, amido groups, thioester groups, ether groups, thioether groups, nitro groups, cyano groups, amino groups, di($C_1$–$C_4$)-alkylamino groups, [dihydroxy-($C_2$–$C_4$)-alkyl]amino groups, [($C_1$–$C_4$)-hydroxyalkyl]-($C_1$–$C_4$)-alkyl-amino groups, trifluromethyl groups, or phosphate groups;

X and Z are equal or different and, independently of each other, denote a branched or unbranched —$(CH_2)_n$— group with n equal to an integer from 1 to 20; a branched or unbranched —$(CH_2)_m$—(CH=CH)$_p$—$(CH_2)_q$ alkene chain with m and q, independently of each other, denoting an integer from 0 to 20 and p denoting an integer from 1 to 5 or a branched or unbranched —(CH$_2$)$_m$—(C≡C)$_p$—(CH$_2$)$_q$-alkyne chain with m and q, independently of each other, denoting an integer from 0 to 20 and p denoting an integer from 1 to 3; and Y denotes an —O—, —S—, —NH—, NR—, or a —C(O)—O—, —O—C(O)—, —C(O)—NH, or —O—C=NH-group; or wherein the —X—(Y)$_r$ Z group optionally denotes a saturated cycloalkane group with 3 to 7 atoms and, depending on group size, optionally contains up to three heteroatoms selected from the group consisting of nitrogen, oxygen, and sulfur; a cycloalkene group with up to two cumulated or non-cumulated double bonds with 3 to 7 atoms and, depending on group size, up to three heteroatoms selected from the group consisting of nitrogen, oxygen, and sulfur; and with the proviso that in formula (I), when R6 denotes a —CH=CH—CHO group or a —CHO group, at least two adjacent R1 to R5 groups form an —O—CH$_2$—O— bridge and with the proviso that in formula (II), when R denotes a -CR7R8R9 group, at least one of R7, R8 and R9 denotes other than hydrogen atom.

2. The agent as defined in claim 1, wherein R6 denotes the —X(Y)$_r$-Z-CHO group with r =0 or 1; and wherein —X(Y)$_r$-Z- denotes a branched or unbranched —(CH$_2$)— group with n equal to an integer from 1 to 10; a branched or unbranched —(CH$_2$)$_m$—(CH=CH)$_p$—(CH$_2$)$_q$-alkene chain wherein a sum of m and q is less then or equal to 12 and p denotes an integer from 1 to 3; a branched or unbranched —(CH$_2$)$_m$—(C≡C)$_p$—(CH$_2$)$_q$-alkyne chain wherein a sum of m and q is less than or equal to 12 and p denotes an integer from 1 to 3; a saturated cycloalkane group with 5 to 6 atoms that optionally contains up to three heteroatoms selected from the group consisting of nitrogen, oxygen, and sulfur; a cycloalkene group with up to two cumulated or non-cumulated double bonds with from 5 to 6 atoms, which, besides carbon atoms and depending on group size, include up to three heteroatoms selected from the group consisting of nitrogen, oxygen, and sulfur; wherein the aforesaid groups are optionally substituted with one or more halogen atoms, hydroxyl groups, sulfonic acid groups, carbonyl groups, carboxyl groups, ester groups, amido groups, thioester groups, ether groups, thioether groups, nitro groups, cyano groups, amino groups, di(C$_1$–C$_4$)-alkylamino groups, [dihydroxy-(C$_2$–C$_4$)-alkyl]amino groups, [(C$_1$–C$_4$)-hydroxyalkyl]-(C$_1$–C$_4$)-alkyl-amino groups, trifluromethyl groups, or phosphate groups.

3. The agent as defined in claim 1, wherein R denotes a saturated, optionally substituted cycloalkyl group with 5 or 6 atoms and optionally including up to three heteroatoms selected from the group consisting of nitrogen, oxygen, and sulfur; an optionally substituted cycloalkene group with 5 or 6 atoms and optionally containing up to three cumulated or non-cumulated double bonds and up to three heteroatoms selected from the group consisting of nitrogen, oxygen, and sulfur; or a —CR7R8R9 group wherein each of said R7, R8 and R9, independently of each other, denotes hydrogen, a saturated cycloalkane group with 5 or 6 atoms and optionally including three heteroatoms selected from the group consisting of nitrogen, oxygen, and sulfur; a cycloalkylene group with up to two double bonds and 5 to 6 atoms and, depending on group size, optionally containing up to three heteroatoms selected from the group consisting of nitrogen, oxygen, and sulfur; a branched or unbranched —(CH$_2$)$_n$— group with n equal to an integer from 1 to 10; a branched or unbranched —(CH$_2$)$_m$—(CH=CH)$_p$—(CH$_2$)$_q$-alkene chain wherein the sum of m and q is less than or equal to 12 and p denotes an integer from 1 to 3; or a branched or unbranched —(CH$_2$)$_m$—(C≡C)$_p$—(CH$_2$)$_q$-alkyne chain wherein the sum of m and q is less than or equal to 12 and p denotes an integer from 1 to 3; wherein the foregoing R groups optionally are substituted with one or more halogen atoms, hydroxyl groups, sulfonic acid groups, carbonyl groups, carboxyl groups, ester groups, amido groups, thioester groups, ether groups, thioether groups, nitro groups, cyano groups, amino groups, di(C$_1$–C$_4$)-alkylamino groups, [dihydroxy-(C$_2$–C$_4$)-alkyl]amino groups, [(C$_1$–C$_4$)-hydroxyalkyl]-(C$_1$–C$_4$)-alkyl-amino groups, trifluoromethyl groups, or phosphate groups.

4. The agent as defined in claim 1, wherein said at least one aldehyde compound of the formula (I) or (II) is selected from the group consisting of 3-phenyl-butyraldehyde; p-ter.t.butyl-α-methylhydrocinnamaldehyde; heliotropin; 2-methyl-3-(4'-ethylphenyl)-propionaldehyde; 2-(phenylmethylene)-heptanal; 3-(3'-isopropylphenyl)-butanal; 2-methyl-3-(4'-isopropylphenyl)propionaldehyde; 2-(phenylmethylene)-octanal; phenylethanal; acetaldehyde; propionaldehyde; butanal; pentanal; isopentanal; hexanal; heptanal; octanal; malonic dialdehyde; glutaraldehyde; 2,4-dimethyl-3-cyclohexenecarboxaldehyde; cyclohexanal; 3,7-dimethyl-7-hydroxyoctanal; cis/trans-3,7-dimethyl-2,6-octadienal; 3,7-dimethyl-6-octanal; (E, Z)-2,6-nonadienal; dimethyloctahydro-2-naph-thaldehyde; 2-methylpentanal; 5-hydroxypentanal; 2-ethylhexanal; 3,5,5-trimethylhexanal; 2-ethylbutyraldehyde; 3,3-dimethylbutyraldehyde; 2-ethylbutyraldehyde; 2-methylbutyraldehyde; isobutyraldehyde; hydroxyisohexyl-3-cyclohexenecarboxaldehyde; 2,6,6-trimethyl-1,3-cyclo-hexadiene-1-carboxaldehyde;and pinoacetaldehyde.

5. The agent as defined in claim 1, containing a total amount of from 0.005 to 20 wt. % of said at least one aldehyde compound of the formula (I) or (II).

6. The agent as defined in claim 1, wherein said at least one developer substance is selected from the group consisting of 1,4-diaminobenzene; 1,4-diamino-2-methylbenzene; 1,4-diamino-2,6-dimethylbenzene; 1,4-diamino-3,5-diethylbenzene; 1,4-diamino-2,5-dimethylbenzene; 1,4-diamino-2,3-dimethylbenzene; 2-chloro-1,4-diaminobenzene; 1,4-diamino-2-(thiophen-2-yl)-benzene; 1,4-diamino-2-(thiophen-3-yl)benzene; 1,4-diamino-2-(pyndin-3-yl)-benzene; 2,5-diaminobiphenyl; 1,4-diamino-2-methoxymethylbenzene; 1,4-diamino-2-aminomethylbenzene 1,4-diamino-2-hydroxyrnethylbenzene; 1,4-diamino-2-(2-hydroxyethoxy)benzene; 2-[2-(acetylamino)ethoxy]-1,4-diaminobenzene; 4-phenylaminoaniline; 4-dimethylaminoaniline; 4-diethylaminoaniline; 4-dipropyl-aminoaniline; 4-[ethyl-(2-hydroxyethyl)amino]-aniline; 4-[di(2-hydroxyethyl)amino]-aniline; 4-[di(2-hydroxyethyl)amino]-2-methylaniline; 4-[(2-methoxyethyl)amino]-aniline; 4-[(3-hydroxypropyl)-amino]aniline; 4-[(2,3-dihydroxypropyl)amino]-aniline; 1,4-diamino-2-(1-hydroxyethyl)-benzene; 1,4-diamino-2-(2-hydroxy-ethyl)benzene; 1,4-diamino-2-(1-methylethyl)benzene; 1,3-bis-[(4-aminophenyl)-(2-hydroxy-ethyl)amino]-2-propanol; 1,4-bis-[(4-aminophenyl)amino]-butane; 1,8-bis-(2,5-diaminophenoxy)-3,6-dioxaoctane; 4-aminophenol; 4-amino-3-methyiphenol; 4-amino-3-(hydroxymethyl)phenol; 4-amino-3-fluorophenol; 4-methylaminophenol; 4-amino-2-(aminomethyl)phenol; 4-amino-2-(hydroxy-methyl)-phenol; 4-amino-2-fluorophenol; 4-amino-2-[(2-hydroxyethyl)amino]-methyiphenol; 4-amino-2-methylphenol; 4-amino-2-(methoxymethyl)phenol; 4-amino-2-(2-hydroxyethyl)phenol; 5-aminosalicyclic acid; 2,5-diaminopyridine; 2,4,5,6-tetraaminopyrimidine; 2,5,6-triamino-4-(1H)-pyrimidone; 4,5-diamino-1 -(2-hydroxyethyl)-1H-pyrazole; 4,5-diamino-1-(1-methylethyl)-1H-pyrazole; 4,5-diamino-1-[(4-methylphenyl)methyl]-1H-pyrazole; 1-[(4-chlorophenyl)methyl]-4,5-diamino-1H-pyrazole; 4,5-diamino-1-methyl-1H-pyrazole; 2-aminophenol; 2-amino-6-methylphenol; 2-amino-5-methylphenol; and 1,2,4-trihydroxybenzene.

7. The agent as defined in claim 1, containing from 0.005 to 20 weight percent of said at least one developer substance and from 0.005 to 20 weight percent of said at least one coupler substance, based on a total amount of ready-to-apply colorant.

8. The agent as defined in claim 1, further comprising at least one direct dye compound.

9. The agent as defined in claim 1, having a pH of from 6.5 to 11.5.

10. The agent as defined in claim 1, consisting of a hair colorant.

11. A ready-to-apply colorant for oxidative dyeing of hair, said colorant comprising an oxidant and said at least one aldehyde compound of the formula (I) or (II) as defined in claim 1.

12. The ready-to-apply colorant as defined in claim 11, wherein said oxidant is hydrogen peroxide.

13. A method of oxidative dyeing of hair, said method comprising the steps of:
a) preparing a ready-to-apply hair dyeing mixture; and
b) applying the ready-to-apply hair dyeing mixture to the hair in an amount sufficient for the dyeing of the hair, depending on the fullness of the hair;
wherein said ready-to-apply hair dyeing mixture comprises(i) at least one developer substance; (ii) at least one coupler substance;
wherein said at least one coupler substance is selected from the group consisting of N-(3-dimethylaminophenyl)urea; 2,6-diaminopyridine; 2-amino-4-[(2-hydroxyethyl)amino]anisole; 2,4-diamino-1-fluoro-5-methylbenzene; 2,4-diamino-1-methoxy-5-methylbenzene; 2,4-diamino-1-ethoxy-5-methylbenzene; 2,4-diamino-1-(2-hydroxyethoxy)-5-methylbenzene; 2,4-di[(2-hydroxy-ethyl)amino]-1,5-dimethoxybenzene; 2,3-diamino-6-methoxypyridine; 3-amino-6-methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-dihydroxypropoxy)benzene; 1,3-diamino-4-(3-dihydroxypropoxy)benzene; 1,3-diamino-4-(2-methoxyethoxy)-benzene; 2,4-diamino-1,5-di(2-hydroxyethoxy)benzene; 1-(2-aminoethoxy)-2,4-diaminobenzene; 2-amino-1-(2-hydroxyethoxy)-4-methylaminobenzene; 2,4-diaminophenoxyacetic acid; 3-[di(2-hydroxyethyl)amino]aniline; 4-amino-2-di[(2-hydroxyethyl)amino]-1-ethoxybenzene; 5-methyl-2-(1-methylethyl)phenol; 3-[(2-hydroxyethyl)amino] aniline; 3-[(2-aminoethyl)amino]aniline; 1,3-di-(2,4-diaminophenoxy)propane; di(2,4-diaminophenoxy) methane; 1,3-diamino-2,4-dimethoxybenzene; 2,6-bis-(2-hydroxyethyl)aminotoluene; 4-hydroxyindole; 3-dimethylaminophenol; 3-diethylaminophenol; 5-amino-2-methyiphenol; 5-amino-4-fluoro-2-methylphenol; 5-amino-4-methoxy-2-methyl-phenol; 5-amino-4-exthoxy-2-methylphenol; 3-amino-2,4-dichlorophenol; 5-amino-2,4-dichlorophenol; 3-amino-2-methylphenol; 3-amino-2-chloro-6-methyiphenol; 3-aminophenol; 2-[(3-hydroxyphenyl)amino]-acetamide; 5-[(2-hydroxyethyl)amino]-4-methoxy-2-methylphenol; 5-[(2-hydroxyethyl)amino]-2-methylphenol; 3-[(2-hydroxyethyl)amino]-phenol; 3-[(2-methoxyethyl)amino]-phenol; 5-amino-2-ethylphenol; 5-amino-2-methoxyphenol; 2-(4-amino-2-hydroxyphenoxy)ethanol; 5-[(3-hydroxypropyl)-amino]-2-methylphenol; 3-[(2,3-dihydroxypropyl)amino]-2-methylphenol; 3-[(2-hydroxyethyl)amino]-2-methylphenol; 2-amino-3-hydroxypyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxy-naphthalene; 2,3-dihydroxynaphthalene; 2,7-dihydroxynaphthalene; 2-methyl-1-naphthol acetate; (m-dihydroxyphenyl)acrylamide; 1-chloro-2,4-dihydroxy-benzene; 2-chloro-(m-dihydroxyphenyl)acrylamide; 1,2-dichloro-3,5-dihydroxy-4-methylbenzene; 1,5-dichloro-2,4-dihydroxybenzene; 1,3-dihydroxy-2-methyl-benzene; 3,4-methylenedioxyphenol; 3,4-methylenedioxyaniline; 5-[(2-hydroxyethyl)-amino]-1,3-benzodioxole; 6-bromo-1-hydroxy-3,4-methylenedioxybenzene; 3,4-diaminobenzoic acid; 3,4-dihydro-6-hydroxy-1,4(2H)-banzoxazine; 6-amino-3,4-dihydro-1,4(2H)benzoxazine; and 3-methyl-1-phenyl-5-pyrazolone; and
(iii) at least one aldehyde compound of formula (I) or (II):

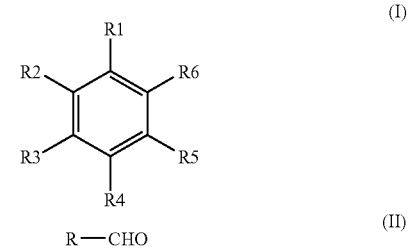

wherein R1, R2, R3, R4, and R5, independently of each other, denote hydrogen, a carboxyl group, an aldehyde group, a halogen atom, a cyano group, a hydroxyl group, a $(C_1–C_4)$-alkoxy group, a $(C_2–C_4)$-hydroxyalkoxy group, a $(C_1–C_6)$-alkyl group, a nitro group, a $(C_1–C_4)$-alkylamino group, a di$(C_1–C_4)$-alkylamino group, a $[(C_2–C_4)$-dihydroxyalkyl)]amino group, a $[(C_1–C_4)$-hydrnxyalkyl]-$(C_1–C_4)$ -alkylamino group, a trifluoromethyl group, a $(C_1–C_4)$-hydroxyalkyl group, or a $(C_2–C_4)$-dihydroxyalkyl group, or two adjacent R1 to R5 groups form an —O—$CH_2$—O— bridge;
R6 denotes a —CH═CH—CHO group, a —CHO group, or a —X(Y)$_r$-Z-CHO group with r=0 or 1;
R denotes a —CR7R8R9 group; a saturated, optionally substituted cycloalkyl group with 3 to 10 atoms and optionally containing up to three heteroatoms selected from the group consisting of nitrogen, oxygen, and sulfur; or an optionally substituted cycloalkylene group with 3 to 10 atoms and optionally containing up to three cumulated or non-cumulated double bonds and up to three heteroatoms selected from the group consisting of nitrogen, oxygen, and sulfur; R7, R8, and R9 are the same or different and, independently of each other, denote hydrogen, a saturated cycloalkyl group with 3 to 10 atoms and optionally containing up to 3 heteroatoms selected from the group consisting of nitrogen, oxygen, and sulfur; a cycloalkylene group with 3 to 10 atoms and optionally containing up to three cumulated or non-cumulated double bonds and up to three heteroatoms selected from the group consisting of nitrogen, oxygen, and sutfur; a branched or unbranched —$(CH_2)_n$— group with n equal to an integer from 1 to 20; a branched or unbranched —$(CH_2)_m$—$(CH=CH)_p$—$(CH_2)_q$-alkene chain with m and q, independently of each other, denoting an integer from 0 to 20 and p denoting an integer from 1 to 5; or a branched or unbranched —$(CH_2)_m$—$(C\equiv C)_p$—$(CH_2)_q$-alkyne chain with m and q, independently of each other, denoting an integer from 0 to 20 and p denoting an integer from 1 to 3; wherein the foregoing R groups are optionally substituted with one or more halogen atoms, hydroxyl groups, sulfonic acid groups, carbonyl groups, carboxyl groups, ester groups, amido groups, thioester groups, ether groups, thioether groups, nitro groups, cyano groups. amino groups, di($C_1$–$C_4$)-alkylamino groups, [dihydroxy-($C_2$–$C_4$)-alkyl]amino groups, [($C_1$–$C_4$)-hydroxyalkyl]-($C_1$–$C_4$)-alkyl-amino groups, trifluromethyl groups, or phosphate groups;

X and Z are equal or different and, independently of each other, denote a branched or unbranched —$(CH_2)_n$— group with n equal to an integer from 1 to 20; a branched or unbranched —$(CH_2)_m$—$(CH=CH)_p$—$(CH_2)_q$-alkene chain with m and q, independently of each other, denoting an integer from 0 to 20 end p denoting an integer from 1 to 5; or a branched or unbranched —$(CH_2)_m$—$(C\equiv C)_p$—$(CH_2)_q$-alkyne chain with m and q, independently of each other, denoting an integer from 0 to 20 and p denoting an integer from 1 to 3; and Y denotes an —O—, —S—, —NH—, NR—, or a —C(O)—O—, —O—C(O)—, —C(O)—NH, or —O—C=NH— group; or wherein the —X—(Y)$_r$Z group optionally denotes a saturated cycloalkane group with 3 to 7 atoms and, depending on group size, optionally contains up to three heteroatoms selected from the group consisting of nitrogen, oxygen, and sulfur; a cycloalkene group with up to two cumulated or non-cumulated double bonds with 3 to 7 atoms and, depending on group size, up to three heteroatoms selected from the group consisting of nitrogen, oxygen, and sulfur; and with the proviso that in formula (I), when R6 denotes a —CH=CH—CHO group or a —CHO group, at least two adjacent R1 to R5 groups form an —O—$CH_2$—O— bridge and with the proviso that in formula (II), when R denotes a —CR7R8R9 group, at least one of R7, R8 and R9 denotes other than hydrogen atom.

14. The method as defined in claim 13, further comprising adding an oxidizing agent to the ready-to-apply hair dyeing mixture prior to the applying.

* * * * *

UNITED STATES PATENT AND TRADEMARK OFFICE
CERTIFICATE OF CORRECTION

| | | |
|---|---|---|
| PATENT NO. | : 7,132,000 B2 | |
| APPLICATION NO. | : 10/486548 | |
| DATED | : November 7, 2006 | |
| INVENTOR(S) | : H. Muerner et al. | |

It is certified that error appears in the above-identified patent and that said Letters Patent is hereby corrected as shown below:

COLUMN 11, CLAIM 1, LINE 67, ADD TEXT AS FOLLOWS.

1,3-diamino-2, 4-dimethoxybenzene; 2,6-bis-(2-hydroxyethyl)aminotoluene;

4-hydroxyindole; 3-dimethylaminophenol; 3-diethylaminophenol;

5-amino-2-methylphenol; 5-amino-4-fluoro-2-methylphenol;

5-amino-4-methoxy-2-methylphenol; 5-amino-4-exthoxy-2-methylphenol;

3-amino-2, 4-dichlorophenol; 5-amino-2, 4-dichlorophenol; 3-amino-2-methylphenol;

3-amino-2-chloro-6-methylphenol; 3-aminophenol; 2-[(3-hydroxyphenyl)amino]-acetamide; 5-[(2-hydroxyethyl)amino]-4-methoxy-2-methylphenol;

5-[(2-hydroxyethyl)amino]-2-methylphenol; 3-[(2-hydroxyethyl)amino]- phenol;

3-[(2-methoxyethyl)amino]-phenol; 5-amino-2-ethylphenol; 5-amino-2-methoxyphenol;

2-(4-amino-2-hydroxyphenoxy)ethanol; 5-[(3-hydroxypropyl)-amino]-2-methylphenol;

3-[(2,3-dihydroxypropyl)amino]-2-methylphenol; 3-[(2-hydroxyethyl)amino]-2-methylphenol; 2-amino-3-hydroxypyridine; 2,6-dihydroxy-3, 4-dimethylpyridine;

5-amino-4-chloro-2-methylphenol; 1-naphthol; 2-methyl-l-naphthol;

1,5-dihydroxynaphthalene; 1,7-dihydroxy-naphthalene; 2,3-dihydroxynaphthalene;

2,7-dihydroxynaphthalene; 2-methyl-1-naphthol acetate;

(m-dihydroxyphenyl)acrylamide; 1-chloro-2,4-dihydroxy-benzene;

2-chloro-(m-dihydroxyphenyl)acrylamide; 1,2-dichloro-3,5-dihydroxy-4-methylbenzene; 1,5-dichloro-2,4-dihydroxybenzene; 1,3-dihydroxy-2-methyl-benzene;

3,4-methylenedioxyphenol; 3,4-methylenedioxyaniline;

UNITED STATES PATENT AND TRADEMARK OFFICE
CERTIFICATE OF CORRECTION

PATENT NO. : 7,132,000 B2
APPLICATION NO. : 10/486548
DATED : November 7, 2006
INVENTOR(S) : H. Muerner et al.

It is certified that error appears in the above-identified patent and that said Letters Patent is hereby corrected as shown below:

5-[(2-hydroxyethyl)-amino]-1,3-benzodioxole; 6-bromo-1-hydroxy-3,4-methylenedioxybenzene; 3,4-diaminobenzoic acid; 3,4-dihydro-6-hydroxy-1,4(2H)-benzoxazine; 6-amino-3,4-dihydro-1,4(2H)benzoxazine; and 3-methyl-1-phenyl-5-pyrazolone; and (iii) at least one aldehyde compound of formula (I) or (II):

Signed and Sealed this

Thirteenth Day of November, 2007

JON W. DUDAS
*Director of the United States Patent and Trademark Office*